(12) United States Patent
Paterson (10) Patent No.: US 6,855,320 B2
(45) Date of Patent: Feb. 15, 2005

(54) FUSION OF NON-HEMOLYTIC, TRUNCATED FORM OF LISTERIOLYSIN O TO ANTIGENS TO ENHANCE IMMUNOGENICITY

(75) Inventor: Yvonne Paterson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 126 days.

(21) Appl. No.: 09/537,642

(22) Filed: Mar. 29, 2000

(65) Prior Publication Data

US 2002/0028206 A1 Mar. 7, 2002

(51) Int. Cl.[7] .................. A61K 39/02; A61K 39/09; A61K 39/295; A61K 39/385
(52) U.S. Cl. ................. 424/192.1; 424/190.1; 424/193.1
(58) Field of Search ............ 424/190.1, 192.1, 424/193.1, 200.1; 435/69.7; 536/23.1; 514/2

(56) References Cited

U.S. PATENT DOCUMENTS 5,262,177 A * 11/1993 Brown et al.
5,830,702 A   11/1998 Portnoy et al. ............ 435/69.3

FOREIGN PATENT DOCUMENTS

WO     WO 99/10496     4/1999

OTHER PUBLICATIONS

Verma et al, Vaccine 13(2): 142–50. Feb 1995.*
Ngo et al., 1994, The Protein Folding Problem and Tertiary Structure Prediction, pp. 492–495.*
Stryer et al, in Biochemistry, Third edition, W H Freeman Company, New York, pp. 31–33, 1998.*
Mikayama et al, Molecular cloning and functional expression of a cDNA encoding gycosylation–inhibiting factor, Nov 1993, Pro Natl. Acad. Sci, USA vol. 90: 10056–10060.*
Skolnick et al., From genes to protein structure and function: novel applications of computational approaches in the genomic era, Jan 2000, Trends in Biotech. 18(1): 34–39.*
Makela et al, Hand book of Experimental Immunology vol. 1, chapter 3, pp. 3.1–3.13; 1987.*
Safley et al, J Immunology 146(10): 3604–3616; May 1991.*
Bielecki J. et al., "*Bacillus subtilis* expressing a haemolysin gene from Listeria monocytogenes can grow in mammalian cells", *Nature* 1990 345:175–176.
Gentschev et al., "*Salmonella* Strain Secreting Active Listeriolysin Changes Its Intracellular Localization", *Infect. Immun*. 1995 63:4202–4205.
Ikonomidis et al., "Delivery of a Viral Antigen to the Class I Processing and Presentation pathway by *Listeria monocytogenes*", *J. Exp. Med*. 1994 180:2209–2218.
Kaufmann, S.H. and Hess, *J*., "Impact of intracellular location of and antigen display by intracellular bacteria: implications for vaccine development", *Immunol. Lett*. Jan. 1999 65(1–2):81–4.
Lin et al., "Treatment of Established Tumors with a Novel Vaccine That Enhances Major Histocompatibility Class II Presentation of Tumor Antigen[1]", *Cancer Res*. 1996 56:21–6.
Pan et al., "Regression of Established Tumors in Mice Mediated by the Oral Administration of a Recombinant *Listeria monocytogenes* Vaccine [1]", *Cancer Res*. 55:4776–4779.
Tanabe et al., "Induction of Protective T cells against *Listeria monocytogenes* Mice by Immunization with a Listeriolysin O–Negative Avirulent Strain of Bacteria and Liposome–Encapsulated Listeriolysin O", J. Immunology 67(2): 568–575, 1999.
Wu et al., "Engineering an itracellular pathway for major histocompatibility complex class II presentation of antigens", *Proc. Natl. Acad. Sci. USA* 1995 92:11671–5.

* cited by examiner

*Primary Examiner*—Christina Chan
*Assistant Examiner*—Phuong Huynh
(74) *Attorney, Agent, or Firm*—Morgan, Lewis & Bockius, LLP (57) ABSTRACT

Methods for enhancing the immunogenicity of an antigen via fusion to a non-hemolytic truncated form of listeriolysin O are provided.

1 Claim, 5 Drawing Sheets

SEQUENCE LISTING

<160> NUMBER OF SEQ ID NOS: 2

<210> SEQ ID NO 1
<211> LENGTH: 529
<212> TYPE: PRT
<213> ORGANISM: Listeria monocytogenes

<400> SEQUENCE: 1

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350
```

-continued

```
Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
        370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Ser Lys Ala Tyr Thr Asp
                405                 410                 415

Gly Lys Ile Asn Ile Asp His Ser Gly Gly Tyr Val Ala Gln Phe Asn
                420                 425                 430

Ile Ser Trp Asp Glu Val Asn Tyr Asp Pro Gly Asn Glu Ile Val
        435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
                500                 505                 510

Gly Thr Thr Leu Tyr Pro Lys Tyr Ser Asn Lys Val Asp Asn Pro Ile
            515                 520                 525

Glu
```

```
<210> SEQ ID NO 2
<211> LENGTH: 416
<212> TYPE: PRT
<213> ORGANISM: Listeria monocytogenes

<400> SEQUENCE: 2

Asp Ala Ser Ala Phe Asn Lys Glu Asn Ser Ile Ser Ser Met Ala Pro
1               5                   10                  15

Pro Ala Ser Pro Pro Ala Ser Pro Lys Thr Pro Ile Glu Lys Lys His
            20                  25                  30

Ala Asp Glu Ile Asp Lys Tyr Ile Gln Gly Leu Asp Tyr Asn Lys Asn
        35                  40                  45

Asn Val Leu Val Tyr His Gly Asp Ala Val Thr Asn Val Pro Pro Arg
    50                  55                  60

Lys Gly Tyr Lys Asp Gly Asn Glu Tyr Ile Val Val Glu Lys Lys Lys
65                  70                  75                  80

Lys Ser Ile Asn Gln Asn Asn Ala Asp Ile Gln Val Val Asn Ala Ile
                85                  90                  95

Ser Ser Leu Thr Tyr Pro Gly Ala Leu Val Lys Ala Asn Ser Glu Leu
            100                 105                 110

Val Glu Asn Gln Pro Asp Val Leu Pro Val Lys Arg Asp Ser Leu Thr
        115                 120                 125

Leu Ser Ile Asp Leu Pro Gly Met Thr Asn Gln Asp Asn Lys Ile Val
    130                 135                 140

Val Lys Asn Ala Thr Lys Ser Asn Val Asn Asn Ala Val Asn Thr Leu
145                 150                 155                 160

Val Glu Arg Trp Asn Glu Lys Tyr Ala Gln Ala Tyr Pro Asn Val Ser
                165                 170                 175

Ala Lys Ile Asp Tyr Asp Asp Glu Met Ala Tyr Ser Glu Ser Gln Leu
            180                 185                 190
```

```
Ile Ala Lys Phe Gly Thr Ala Phe Lys Ala Val Asn Asn Ser Leu Asn
        195                 200                 205

Val Asn Phe Gly Ala Ile Ser Glu Gly Lys Met Gln Glu Glu Val Ile
        210                 215                 220

Ser Phe Lys Gln Ile Tyr Tyr Asn Val Asn Val Asn Glu Pro Thr Arg
225                 230                 235                 240

Pro Ser Arg Phe Phe Gly Lys Ala Val Thr Lys Glu Gln Leu Gln Ala
            245                 250                 255

Leu Gly Val Asn Ala Glu Asn Pro Pro Ala Tyr Ile Ser Ser Val Ala
            260             265                 270

Tyr Gly Arg Gln Val Tyr Leu Lys Leu Ser Thr Asn Ser His Ser Thr
        275                 280             285

Lys Val Lys Ala Ala Phe Asp Ala Ala Val Ser Gly Lys Ser Val Ser
        290             295                 300

Gly Asp Val Glu Leu Thr Asn Ile Ile Lys Asn Ser Ser Phe Lys Ala
305             310                 315                 320

Val Ile Tyr Gly Gly Ser Ala Lys Asp Glu Val Gln Ile Ile Asp Gly
            325                 330                 335

Asn Leu Gly Asp Leu Arg Asp Ile Leu Lys Lys Gly Ala Thr Phe Asn
            340                 345                 350

Arg Glu Thr Pro Gly Val Pro Ile Ala Tyr Thr Thr Asn Phe Leu Lys
        355                 360                 365

Asp Asn Glu Leu Ala Val Ile Lys Asn Asn Ser Glu Tyr Ile Glu Thr
        370             375                 380

Thr Ser Lys Ala Tyr Thr Asp Gly Lys Ile Asn Ile Asp His Ser Gly
385                 390                 395                 400

Gly Tyr Val Ala Gln Phe Asn Ile Ser Trp Asp Glu Val Asn Tyr Asp
                405             410                 415
```

FUSION OF NON-HEMOLYTIC, TRUNCATED FORM OF LISTERIOLYSIN O TO ANTIGENS TO ENHANCE IMMUNOGENICITY

This invention was supported in part by funds from the U.S. government (NIH Grant No. CA69632) and the U.S. government may therefore have certain rights in the invention.

BACKGROUND OF THE INVENTION

Stimulation of an immune response is dependent upon the presence of antigens recognized as foreign by the host immune system. Bacterial antigens such as *Salmonella enterica* and *Mycobacterium bovis* BCG remain in the phagosome and stimulate CD4 T-cells via antigen presentation through major histocompatibility class II molecules. In contrast, bacterial antigens such as *Listeria monocytogenes* exit the phagosome into the cytoplasm. The phagolysosomal escape of *L. monocytogenes* is a unique mechanism which facilitates major histocompatibility class I antigen presentation of listerial antigens. This escape is dependent upon the pore-forming sulfhydryl-activated cytolysin, listeriolysin O (LLO).

The ability of *L. monocytogenes* to break down the vacuole within a host cell and enter the cytoplasm has led to its use as a recombinant vaccine. U.S. Pat. No. 5,830,702 describes vaccines comprising attenuated mutants of *Listeria* spp. genetically engineered to express foreign antigens in the cytoplasm of infected macrophages and other cells. Several approaches for expressing the antigen in *Listeria* spp. are described including generation of a fusion protein of a selected foreign antigen and a listerial protein, preferably an enzyme involved in lysis of host vacuoles. In particular, a fusion protein encoding the hly promoter and the first 416 amino acids of LLO fused in-frame to the entire coding sequence of the NP antigen was constructed in *E. coli* and on transformation to *Listeria monocytogenes* is demonstrated to secrete a 105 kDA protein that reacts with antiserum to LLO and NP (col. 24 of '702 patent). Recombinant *L. monocytogenes* secreting a fusion protein comprising listeriolysin O and NP (LLO-NP) was demonstrated to target infected cells for lysis by NP-specific class I-restricted cytotoxic T cells. In contrast, a hemolysin-negative *L. monocytogenes* strain expressing LLO-NP presented the antigen in a class II restricted manner (Ikonimidis et al. *J. Exp. Med.* 1994 180:2209–2218). Thus, from these studies it was surmized that hemolysin-dependent bacterial escape from the vacuole is necessary for class I presentation in vitro.

The escape function of *L. monocytogenes* has also been transferred to *Bacillus subtilis* and attenuated *Salmonella* ssp. strains (Bielecki, J. et al. *Nature* 1990 345:175–176, Gentschev et al. *Infect. Immun.* 1995 63:4202–4205). S. enteric and *M. bovis* BCG vaccine carriers which secrete listeriolysin O have also been constructed (Kaufmann, S. H. and Hess, *J. Immunol. Lett.* January 1999 65(1–2):81-4). These constructs are taught to be capable of introducing antigens into the MHC class II and MHC class I pathway, resulting in stimulation of both CD4 and CD8 T-cells. Comparison of *S. enterica* vaccines which display the same listerial antigen in secreted and somatic form showed the secreted antigen display to be superior to the somatic antigen display (Kaufman, S. H. and Hess, *J. Immunol. Lett.* January 1999 65(1–2):81-4).

WO 99/10496 discloses recombinant BCG strains secreting hemolytically active hly with an improved MHC class I-restricted immune response for use as a vaccine against tuberculosis.

Administration of purified listeriolysin O encapsulated in liposomes has also been reported to be effective in the induction of antigen-specific Th1-dependent protective immunity to various kinds of intracellular parasitic bacteria in vivo (Tanabe et al. *Infect. Immun.* February 1999 67(2): 568–75).

It has now been found that the immune response to an antigen can be enhanced by fusion of the antigen to a non-hemolytic truncated form of listeriolysin O (ΔLLO).

SUMMARY OF THE INVENTION

An object of the present invention is to provide a method for enhancing the immunogenicity of an antigen which comprises fusing to the antigen a non-hemolytic truncated form of listeriolysin O (ΔLLO).

DETAILED DESCRIPTION OF THE INVENTION

The present invention relates to a method for enhancing the immunogenicity of a selected antigen by fusion of the selected antigen to a non-hemolytic truncated form of listeriolysin O. It has now been found that fusion of an antigen to a non-hemolytic truncated form of listeriolysin O results in an antigen with enhanced immunogenicity as compared to antigen alone. This truncated form of listeriolysin O fused to an antigen better enables cell mediated immunity and anti-tumor immunity as compared to antigen alone. Further, these fusion proteins need not be expressed by *L. monocytogenes*, but rather can be expressed and isolated from other vectors and cell systems routinely used for protein expression and isolation.

Listeriolysin O (LLO) binds to cholesterol-containing membranes wherein it oligomerizes to form pores. The oligomerization is dependent on the presence of a reduced cystine residue at position 484 in the sequence that is required for oligomerization. The hly gene encodes a protein of 529 residues (GenBank Accession No. P13128; SEQ ID NO:1), the first 25 amino acids are the signal sequence and are cleaved from LLO when it is secreted by the bacterium. Thus, the full length active LLO protein is approximately 504 residues. For purposes of the present invention, by "truncated form of LLO or ΔLLO" it is meant a fragment of LLO which does not contain the activation domain at the amino terminus including cystine 484. Thus, the ΔLLO used in the following experiments was 416 amino acids long (SEQ ID NO:2) as 88 residues from the amino terminus which is inclusive of the activation domain containing cystine 484. However, it is believed that other ΔLLOs without the activation domain, and in particular cystine 484, will also be effective.

Enhanced immunogenicity of an antigen following fusion to a non-hemolytic truncated form of listeriolysin O was demonstrated.

Figure 1:
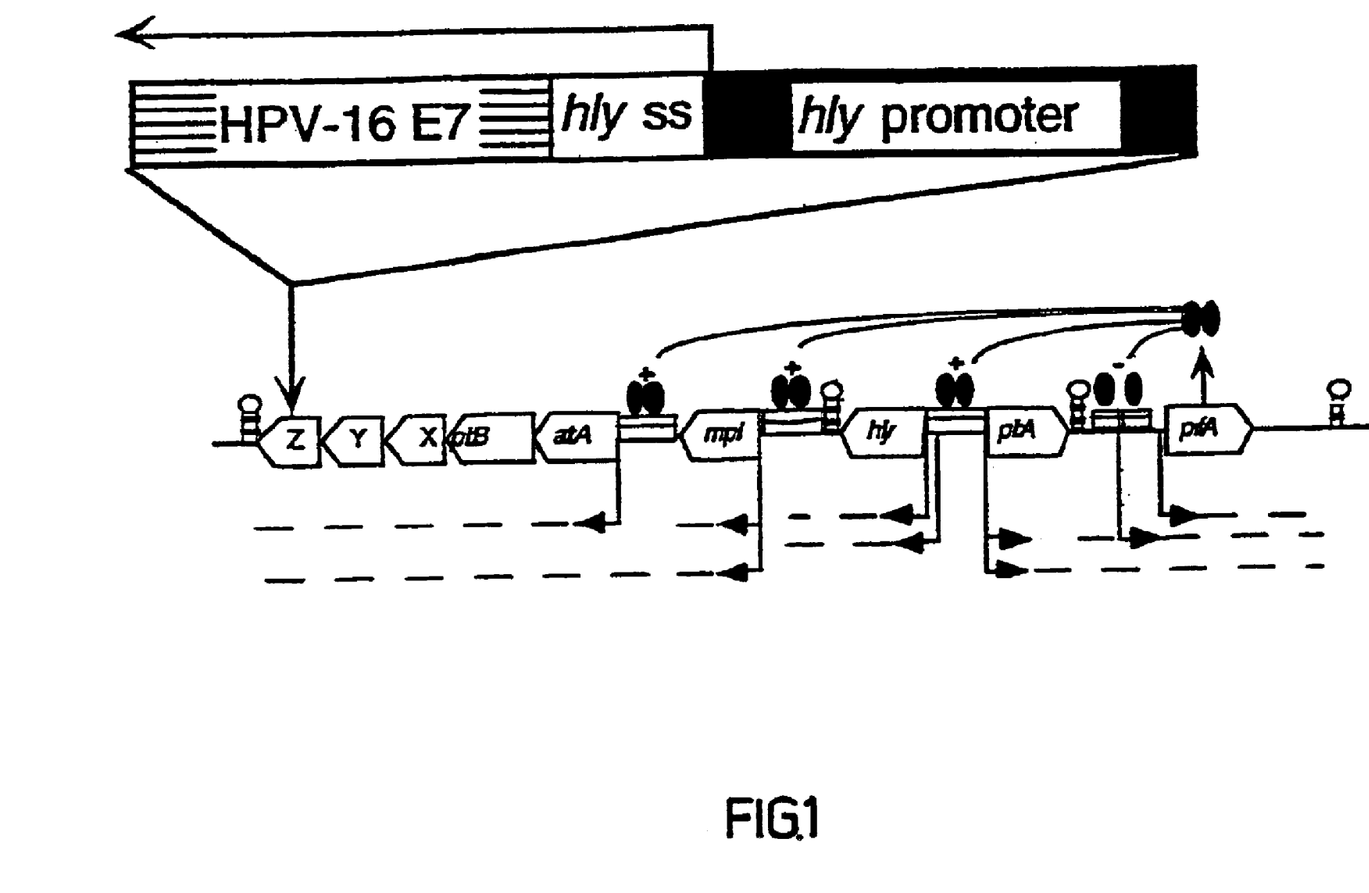
FIG. 1 is a diagram of an HPV-E7 chromosomal expression system constructed by integration of an E7 gene into the *Listeria* chromosome.

In a first set of experiments, the HPV-E7 antigen was expressed in *L. monocytogenes*. An *L. monocytogenes* recombinant that expressed E7 was made by chromosomal integration of the E7 gene under the control of the hly promoter and with the inclusion of the hly signal sequence to ensure secretion of the gene product. The site of integration into the chromosome by homologous recombination was into a region that is non-essential for Lm virulence. The scheme for this is depicted in FIG. 1. The advantage in using this type of transformation is that resulting recombinants are stably transformed and contain no drug selection markers since the CAT gene, included in the plasmid to select for successful transformants after electroporation, is excised during a second recombination event. The expression and secretion of the antigen from the resulting recombinants, Lm-E7, was verified by Western Blot. In addition, therapeutic effects of Lm-E7 were optimized. For example, it was found that the best results were achieved delivering the vaccine orally as compared to parenterally and in a combined protection and regression mode that requires priming with Lm-E7 before tumor challenge and then administering Lm-E7 therapeutically after tumor challenge. Table 1 provides more details for optimized anti-tumor effects observed in this model in three different tumor cell lines, TC-1, C3 and EL-4/E7. Bacteria were delivered orally 14 and 7 days prior to tumor challenge and days 7 and 14 following tumor challenge. Delivery of $10^6$ bacteria intraperitoneally in a similar protocol provided no long-term protection. However, better protection was observed when Lm-E7 was delivered orally. More specifically, with this regimen approximately 50% of the animals remained tumor free in perpetuity and immunization seriously retarded tumor growth in all animals.

TABLE 1

Treatment with Lm-E7

Number of tumor free animals versus total in study (number survived)

| Treatment | $10^5$ TC-1 on day 60 | $10^6$ C3 on day 42 | $5 \times 10^5$ EL-4/E7 on day 40 |
|---|---|---|---|
| $10^8$ Lm-E7 | 3/8 (5) | 4/8 (8) | 4/8 (6) |
| $10^8$ Lm-Gag(ZY-18) | 2/8 (2) | 0/8 (0) | 2/8 (0) |
| Naive | 0/8 (0) | 0/8 (0) | 1/8 (0) |

Animals administered TC-1 or EL-4/E7 tumor cells that were tumor free were re-challenged on day 60 with TC-1 or day 40 EL-4/E7, respectively. The two animals in each group that had been immunized with Lm-Gag grew tumors whereas the animals immunized with Lm-E7 remained tumor free until termination of the experiment (day 124 in the case of TC-1 and day 54 for EL-4/E7).

Compared to results previously disclosed with Lm-NP and the RENCA, CT-26 and B16F10-NP models (Pan et al. 1995), the Lm-E7 was less effective than expected. Accordingly, an Lm-E7 construct was prepared in accordance with the method taught for preparation of the Lm-NP construct of Pan et al. (*Cancer Res.* 1995 55:4776–4779).

Figure 2:
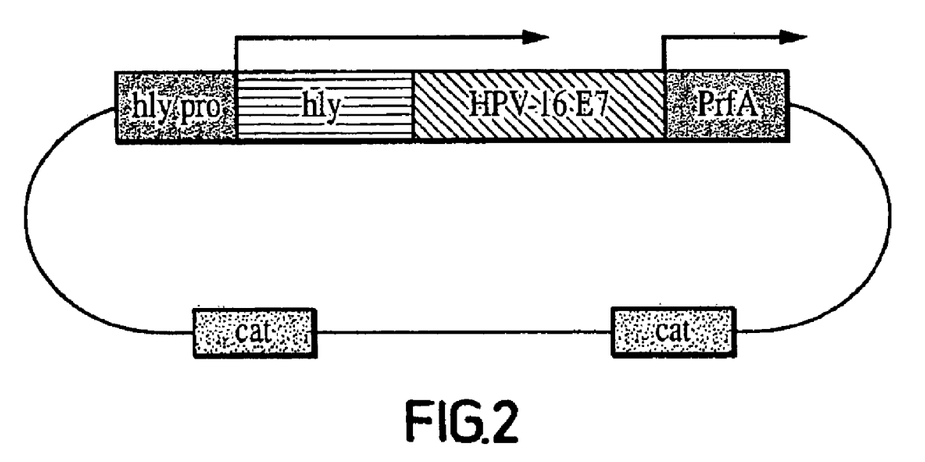
FIG. 2 is a diagram of a preferred multi-copy plasmid containing prfA and E7 fused to a truncated form of the hly gene (Δhyl) that produced ΔLLO.

Specifically, a second *L. monocytogenes* vaccine that expresses a E7 fusion protein, referred to as Lm-LLO-E7, was prepared by complementing a prfA-deletion mutant with a plasmid containing a copy of the prfA gene and a copy of the E7 gene fused to a form of the hly gene truncated to eliminate the hemolytic activity of the enzyme, ΔLLO (see FIG. 2). Functional LLO is maintained by the organism via the endogenous chromosomal copy of hly. The expression and secretion of the fusion protein was verified by Western blot.

The ability of the Lm-LLO-E7 and Lm-E7 vaccine to induce anti-tumor immunity was then compared in a regression model. As shown in Table 2, Lm-LLO-E7 was found to be more effective than Lm-E7.

TABLE 2

Number of mice cured of TC-1 tumor at conclusion of experiment

| Treatment | Mice TC-1 free at day 45 | Mice alive at day 45 | Mice alive at day 134 |
|---|---|---|---|
| Naive | 0/8 | 0/8 | 0/8 |
| Lm-LLO-E7 | 4/8 | 8/8 | 4/8 |
| Lm-E7 | 0/8 | 7/8 | 0/8 |

Thus, expression of the foreign gene as a fusion protein with ΔLLO enhances the immunogenicity of the antigen.

Figure 3:
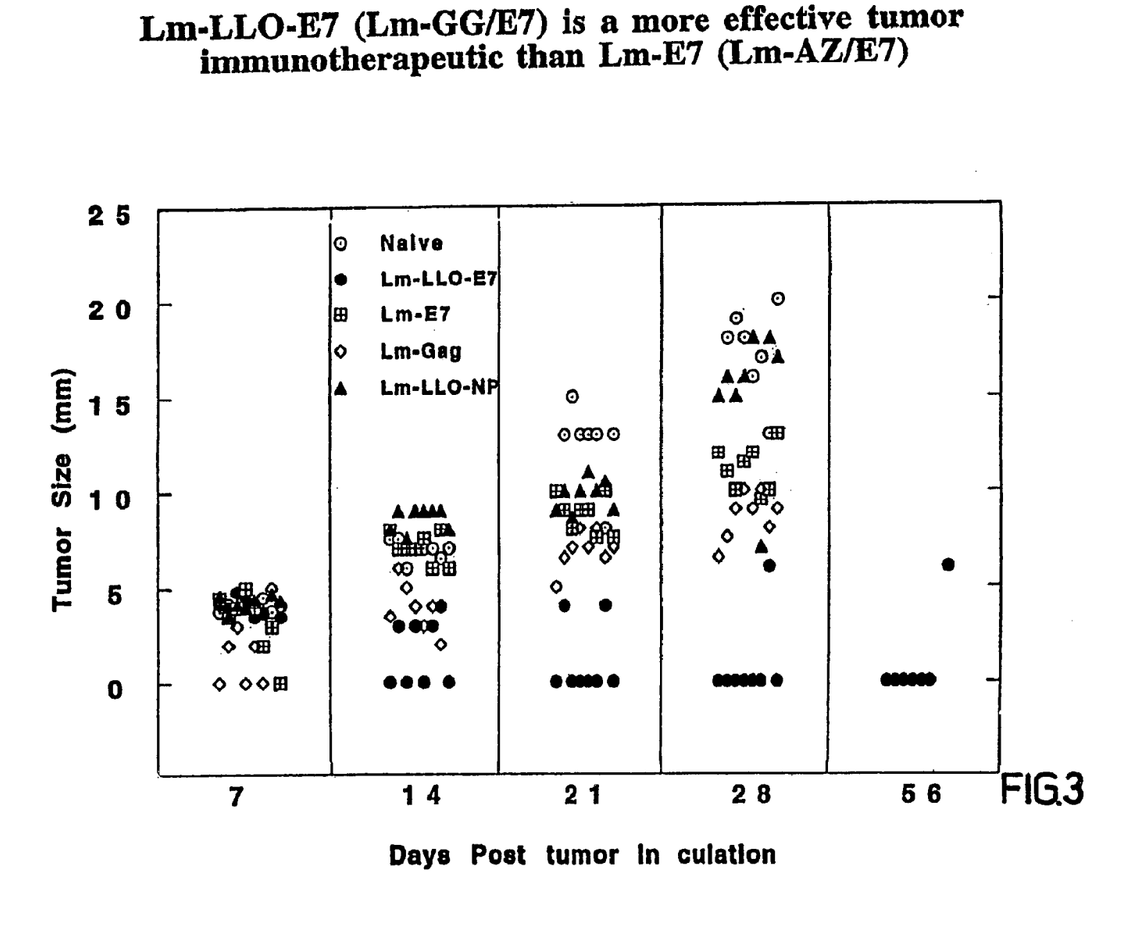
FIG. 3 is a graph showing tumor immunotherapeutic efficacy of antigens expressed in *L. monocytogenes*. Tumor size in millimeters in mice is shown at 7, 14, 21, 28 and 56 days post tumor-inoculation. Naive mice are depicted by an open-circle; mice administered Lm-LLO-E7 are depicted by a filled circle; mice administered Lm-E7 are depicted by a square; mice administered Lm-Gag are depicted by an open diamond; and mice administered Lm-LLO-NP are depicted by a filled triangle.

Additional experiments were performed to compare the ability of Lm-E7 with Lm-LLO-E7 to induce the regression of established sub-cutaneous HPV-16 immortalized tumors from C57Bl/6 mice. Results from these experiments are depicted in FIG. 3. In these experiments, mice were immunized i.p. with 0.1 $LD_{50}$ with one of four constructs, Lm-E7, Lm-Gag (isogenic with Lm-E7 except for the antigen expressed), Lm-LLO-E7 or Lm-LLO-NP. Lm-LLO-NP is isogenic with Lm-LLO-E7 but expresses influenza antigen. A second immunization was performed on day 14. As can be seen in FIG. 3, 6 of 8 mice immunized with Lm-LLO-E7 were cured of their tumors and remained tumor free. None of the other animals showed any regression of the established tumors. Similar results have been achieved for Lm-LLO-E7 under different immunization protocols. Further, just one immunization has been demonstrated to cure mice of established TC-1 of 5 mm diameter.

Additional experiments were performed to confirm the enhanced therapeutic efficacy of a fusion protein comprising the E7 antigen and a truncated form of listeriolysin O. In these experiments a vaccinia vector that expresses E7 as a fusion protein with a non-hemolytic truncated form of listeriolysin O was constructed. The WR strain of vaccinia was used as the recipient and the fusion gene was excised from the listerial plasmid and inserted into pSC11 under the control of the p75 promoter. This vector was chosen because it is the transfer vector used for the vaccinia constructs Vac-SigE7Lamp and Vac-E7 and would therefore allow direct comparison with Vac-LLO-E7. In this way all three vaccinia recombinants would be expressed under control of the same early/late compound promoter p7.5. In addition SC11 allows the selection of recombinant viral plagues to TK selection and β-galactosidase screening.

Figure 5:
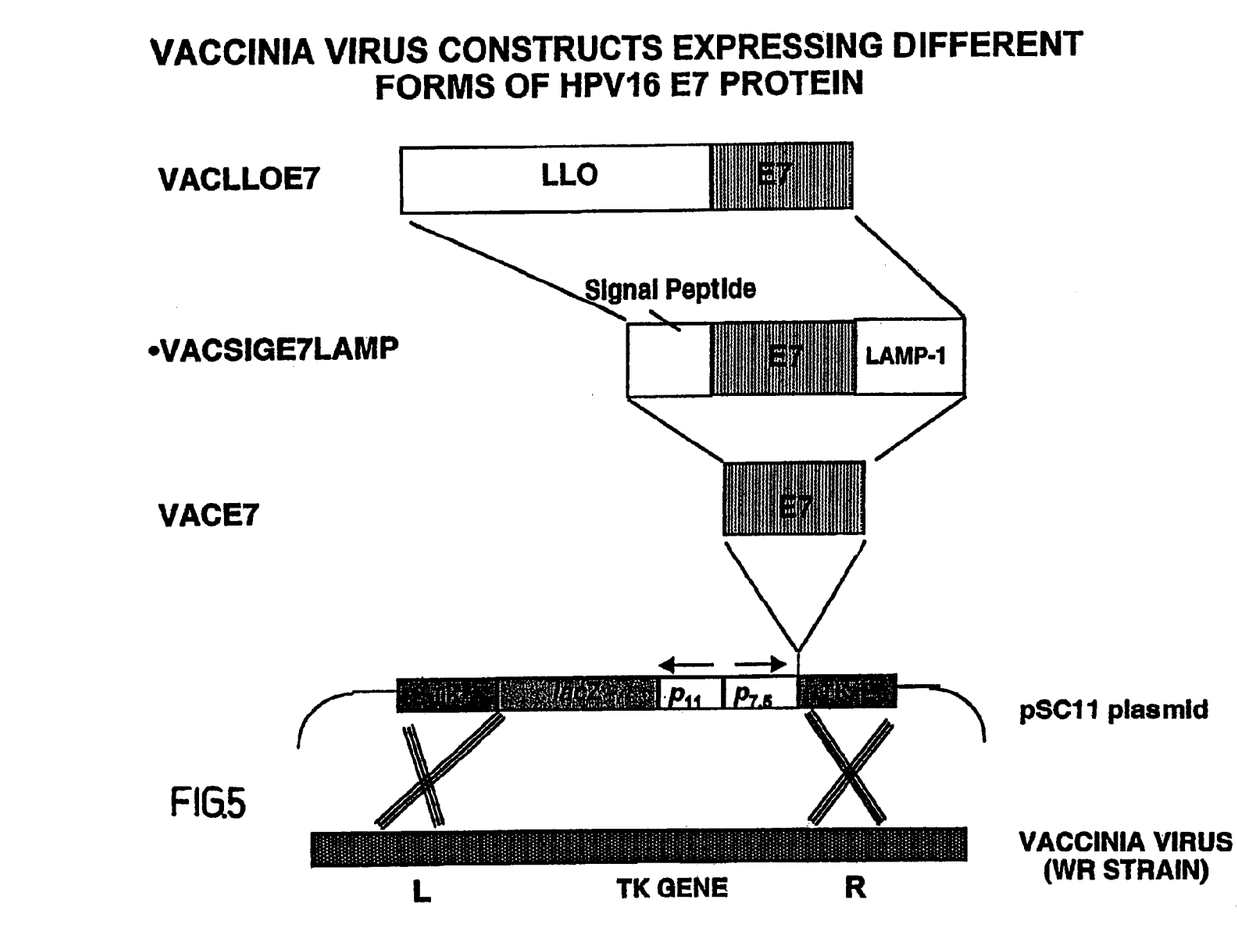
FIG. 5 is a diagram of various *Vaccinia* virus constructs expressing different forms of HPV16 E7 protein.

FIG. 5 shows the various vaccinia constructs used in these experiments. Vac-SigE7Lamp is a recombinant vaccinia virus that expressed the E7 protein fused between lysosomal associated membrane protein (LAMP-1) signal sequence and sequence from the cytoplasmic tail of LAMP-1 (Wu et al. *Proc. Natl. Acad. Sci. USA* 1995 92:11671–5; Lin et al. *Cancer Res.* 1996 56:21–6). It was designed to facilitate the targeting of the antigen to the MHC class II pathway.

The following modifications were made to allow expression of the gene product by vaccinia: (a) the T5XT sequence that prevents early transcription by vaccinia was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resultant pSC11-E7 construct was used to transfect the TK-ve cell line CV1 that had been infected with the wildtype vaccinia strain, WR. Cell lysates obtained from this co-infection/transfection step contain vaccinia recombinants that were plaque purified 3 times. Expression of the LLO-E7 fusion product by plaque purified vaccinia was verified by Western blot using an antibody directed against the LLO protein sequence. In addition, the ability of Vac-LLO-E7 to produce CD8+ T cells specific to LLO and E7 was determined using the LLO(91–99) and E7(49–57) epitopes of Balb/c and C57/BL6 mice, respectively. Results were confirmed in a chromium release assay.

Figure 4:
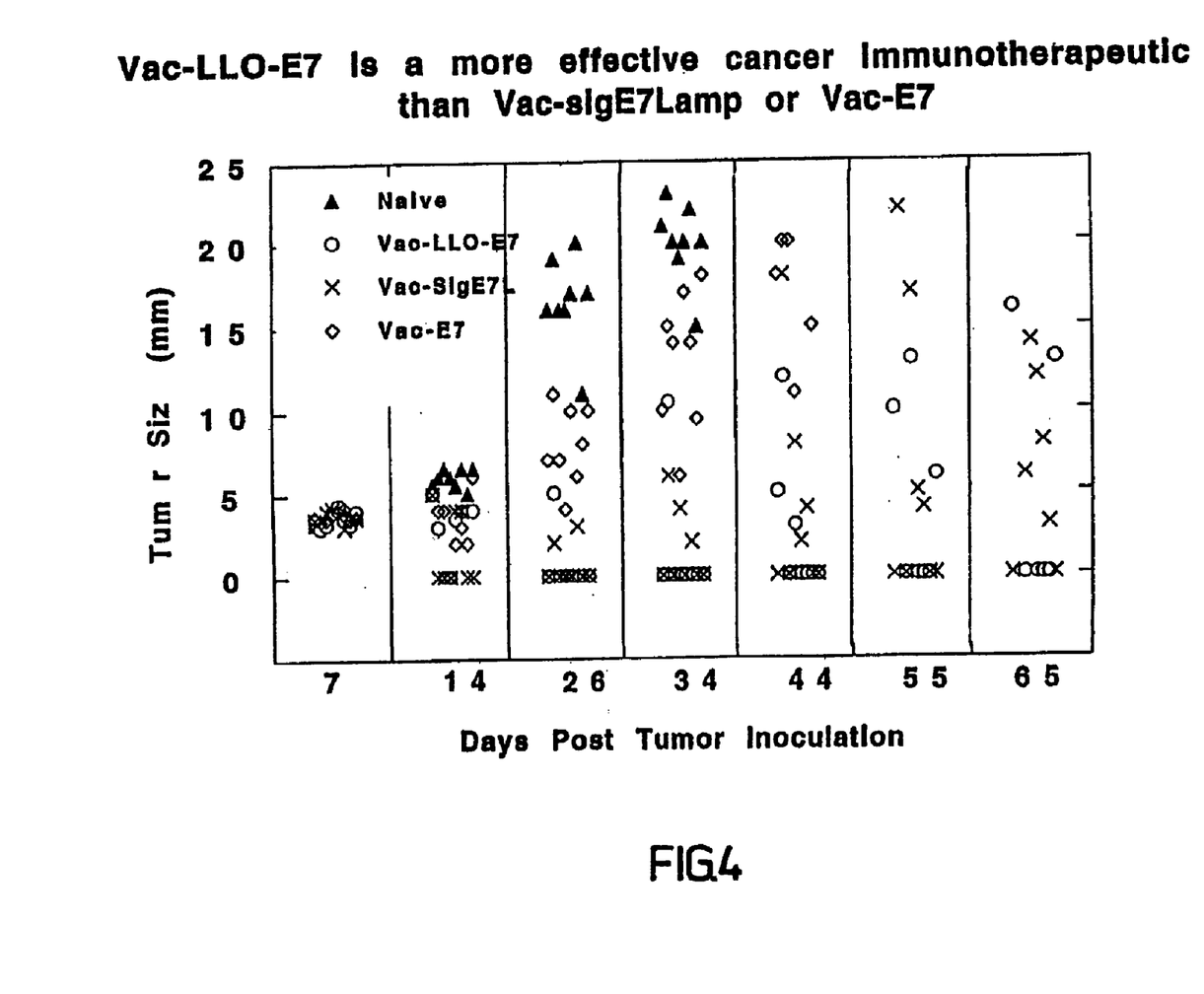
FIG. 4 is a graph showing tumor immunotherapeutic efficacy of antigens expressed by *Vaccinia*. Tumor size in millimeters in mice is shown at 7, 14, 26, 34, 44, 55 and 65 days post tumor-inoculation. Naive mice are depicted by a filled triangle; mice administered Vac-LLO-E7 are depicted by an open circle; mice administered Vac-SigE7L are depicted by an X; and mice administered Vac-E7 are depicted by an open diamond.

Tumor rejection studies were performed with TC-1 following the same protocol as described supra. Two experiments were performed with differing delays before treatment was started. In one experiment, treatments were initiated when the tumors were about 3 mm in diameter (see FIG. 4). As of day 76, 50% of the Vac-LLO-E7 treated mice are tumor free and 25% of the Vac-SigE7Lamp mice are tumor free.

In the second experiment, TC-1 tumors were grown to a larger size (5 to 6 mm). The LLO-E7 fusion protein based vectors were then compared against a larger number of vectors. Although some of the vaccine groups showed significant temporary regression of TC-1, by day 65 the data clearly shows that Lm-LLO-E7 and Vac-LLO-E7 are the most effective vaccines with respect to the ability to permanently induce the regression of established TC-1. Only 12% of the Vac-SigE7Lamp treated mice were tumor free while 37% of the Vac-LLO-E7 and Lm-LLO-E7 mice were tumor free. All other mice were dead.

Thus, expression of the antigen as a fusion protein with a non-hemolytic truncated form of listeriolysin O in host cell systems in listeria and host cell systems other than listeria results in enhanced immunogenicity of the antigen. While comparative experiments were performed with vaccinia, a multitude of other plasmids and expression systems which can be used to express these fusion proteins are known. For example, bacterial vectors useful in the present invention include, but are not limited to *Salmonella* sp., *Shigela* sp., BCG, *L. monocytogenes* and *S. gordonii*. Viral vectors useful in the present invention include, but are not limited to, Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. Naked DNA vectors can also be used.

Accordingly, the present invention provides methods for enhancing the immunogenicity of an antigen via fusion of the antigen to a non-hemolytic truncated form of listeriolysin O or ΔLLO. In a preferred embodiment, the fusion proteins are produced recombinantly via a plasmid which encodes the truncated form of the listeriolysin O and the antigen. However, the antigen may also be chemically conjugated to the truncated form of listeriolysin O. These fusion proteins can then be incorporated into vaccines for administration to animals, preferably humans, to invoke an enhanced immune response against the antigen of the fusion protein. As will be obvious to those of skill in the art upon this disclosure, such vaccines are particularly useful in the treatment of infectious and neoplastic diseases.

These vaccines may further comprise adjuvants. Examples of adjuvants useful in these vaccines include, but are not limited to, unmethylated CpG, quill glycosides, CFA, QS21, monophosphoryl lipid A, liposomes, and bacterial mitogens and toxins.

The following examples are provided for illustrative purposes only and are not intended to limit the invention.

EXAMPLES

Example 1

Tumor Cell Lines

TC-1 is a lung epithelial cell from C57BL/6 mice immortalized by HPV-16 E6 and E7 and transformed by pVEJB expressing activated human c-HA-ras. C3 is a mouse embryo cell frp, C57BL/6 mice immortalized with the complete genome of HPV16 and transformed with pEJ-ras. EL-4/E7 is the thymoma EL-4 retrovirally transduced with E7.

Example 2

Comparison of Efficacy of Lm-GG/E7, Lm-AZ/E7 and Vac-SigE7Lamp

TC-1 ($1 \times 10^5$) or C-3 ($5 \times 10^5$) tumor cells were implanted subcutaneously in mice and allowed to grow for 7 to 9 days by which time they were palpable (~5 mm in size). Mice were then immunized i.p. with one of three constructs, Vac-SigE7Lamp ($10^7$ PFU), Lm-E7 ($10^6$ CFU) or Lm-LLO-E7 ($10^7$ CFU). Animals received Lm-LLO-E7 and LM-E7 on days 7 and 14. Surviving mice were re-challenged with $10^5$ TC-1 on day 43.

Example 3

Comparison of Efficacy of Vac-LLO-E7, Vac-E7 and Vac-SigE7Lamp

Four groups of 8 mice were implanted with $10^5$ cells of TC-1. After 7 days the tumors were approximately 4 mm in size. One group of mice was untreated. Each of the other groups received $10^7$ PFU of either Vac-E7, Vac-LLO-E7 or Vac-Sig-E7-lamp 7. A booster dose was administered on day 14.

Example 4

Comparison of Efficacy of Vac-LLO-E7 and Lm-LLO-E7 with Various other Vectors

TC-1 tumor cells ($2 \times 10^5$) were implanted s.c. on the left flank in 96 C57BL/6 mice and allowed to grow for 7 days. The mice were divided into groups of 8 mice and each group was treated with one of the following vaccine: naive (no vaccine); Vac SigE7Lamp, $10^7$ PFU, i.p.; Vac-LLO-E7, $10^7$ PFU, i.p.; or Lm-LLO-E7, $10^7$ PFU, i.p. The animals received a booster immunization one week later. Tumor growth was followed every two days by caliper measurement and recorded as the average of the narrowest and longest surface length. Immune parameters were also determined.

What is claimed is:

1. A method for enhancing the cell-mediated immunogenicity of a tumor antigen, wherein the cell-mediated immunogenicity comprises major histocompatability class I presentation of the tumor antigen, the method comprising fusing to the tumor antigen a non-hemolytic truncated form of listeriolysin O by recombinant expression of a plasmid encoding the truncated form of the listeriolysin O and the tumor antigen in a host cell other than listeria or by a nonlisteria vector system or by chemical conjugation of the tumor antigen to the truncated form of the listeriolysin O, wherein the amino acid sequence of the non-hemolytic truncated form of listeriolysin O consists the amino acid sequence set forth in SEQ ID NO:2.

* * * * *